United States Patent [19]

Conner, Jr. et al.

[11] Patent Number: 4,472,314

[45] Date of Patent: Sep. 18, 1984

[54] BISMUTH-CONTAINING MIXED OXIDES OF PEROVSKITE STRUCTURE IN OXIDATION OF ACYCLIC HYDROCARBONS

[75] Inventors: William C. Conner, Jr., Montague, Mass.; Stuart L. Soled, Madison, N.J.; Anthony J. Signorelli, Succasunna, N.J.; Bruce A. DeRites, Wayne, N.J.

[73] Assignee: Allied Corporation, Morris Township, Morris County, N.J.

[21] Appl. No.: 153,484

[22] Filed: May 27, 1980

[51] Int. Cl.³ .............. C07C 27/14; C07C 29/50; C07C 45/33; C07C 45/34; C07C 51/215; C07C 51/25
[52] U.S. Cl. .................. 260/413; 260/465.3; 502/215; 502/306; 502/340; 502/525; 549/258; 562/547; 562/549; 568/475; 568/476; 568/481; 568/482; 568/910; 585/651; 585/653
[58] Field of Search .............. 562/549, 547, 512.2; 260/413, 346.75, 398.6; 568/476, 469.9, 479, 475, 481, 482, 910, 910.5; 252/475, 439, 477 R; 549/258; 502/215, 340, 525

[56] References Cited

U.S. PATENT DOCUMENTS 3,806,470  4/1974  Aykan et al. ............. 252/462
4,182,694  1/1980  Lauder .................... 252/462

OTHER PUBLICATIONS

Voorhoeve et al., Science, Mar. 4, 1977, vol. 195, #4281, 827–833.
Schitterhelm et al., Z. Anorg. Alleg. Chem., vol. 425, pp. 175–179, (1976).
Rauser et al., Z. Anorg. Alleg. Chem., vol. 429, pp. 181–184.

*Primary Examiner*—Vivian Garner
*Attorney, Agent, or Firm*—Alan M. Doernberg; Gerhard H. Fuchs; Kenneth E. Stroup, Jr.

[57] ABSTRACT

Mixed oxides of bismuth with other metals of the perovskite structure and having vacant lattice sites in the same lattice positions occupied by bismuth are disclosed as partial oxidation and ammoxidation catalysts. Such oxides are used as catalysts in the improved method of oxidizing an acyclic hydrocarbon of 1–10 carbons having at most one olefinic unsaturation by reacting the acyclic hydrocarbon in the vapor phase with oxygen in the presence of the solid catalyst to form products having carbon, hydrogen and oxygen.

10 Claims, No Drawings

BISMUTH-CONTAINING MIXED OXIDES OF PEROVSKITE STRUCTURE IN OXIDATION OF ACYCLIC HYDROCARBONS

BACKGROUND OF THE INVENTION

The present invention relates to mixed oxides and to their use as catalysts for the partial oxidation or ammoxidation of hydrocarbons.

A number of organic materials of value are produced by oxidizing hydrocarbons with oxygen. Examples are the oxidation of propylene to acrolein, the oxidation of butane to maleic anhydride. Related processes starting with raw materials containing one oxygen only are the oxidation of methanol to formaldehyde and the oxidation of tert-butyl alcohol to methacrolein (an intermediate to methyl methacrylate). Still other processes employ both oxygen and ammonia as reactants such as the ammoxidation of propylene to acrylonitrile. An important criterion is the ability of a catalyst and a process based on the catalyst to form partial oxidation products (having carbon and both hydrogen and oxygen) without producing excessive amounts of completely oxidized products (CO and $CO_2$) or, in the case of hydrocarbon starting materials of more than one carbon, of hydrocarbons of lesser carbon number (i.e. cracking). Other important criteria is to have a process which can be manipulated to reduce the number of different partial oxidation products produced and to maximize the proportion of those produced which are desired. From propane, for example, it may be desired to maximize the production of acetaldehyde and propionaldehyde while minimizing the production of other partial oxidation products such as ethanol, propanol, methanol (except as a by-product of acetaldehyde production) and formaldehyde (except as a by-product of acetaldehyde production).

Mixed oxides of various types have been suggested or used for such oxidations. Examples include the following:

| Catalyst | Process | Reference |
|---|---|---|
| $Fe_2(MoO_4)_3$ | methanol to formaldehyde | K. Weissermel et. al, Ind. Org. Chem. (1978) |
| $Bi_2O_3$—$MoO_3$ | propylene to acrolein | K. Weissermel et. al, Ind. Org. Chem. (1978) |

The use of catalysts of perovskite structure has been suggested by R. J. H. Voorhoeve et. al. in *Science*, vol. 195, pp. 827 et. seq. (1977) and R. J. H. Voorhoeve, pp. 129–180 of *Advanced Materials in Catalysis* (J. L. Burton et. al. eds., Academic Press, 1977). Perovskites are a well-studied class of crystals having two types of cation lattice sites, having A ions occupying dodecahedral coordination sites (12-coordination sites) and B ions occupying octahedral coordination sites (6-coordination sites). Examples of perovskites containing barium, rare earths (e.g. La) and tellurium are disclosed in H. J. Schitterhelm et. al, *Z. Anorg. Alleg. Chem.*, vol. 425, pp. 175 et. seq. (1976) and G. Rauser et. al., *Z. Anorg. Alleg. Chem.*, vol. 429, pp. 181 et. seq. (1977). These references disclose several classes of perovskites having B-site vacancies.

In A. W. Sleight's bismuth-containing scheelite catalysts, the presence of vacancies (also called defects) and bismuth in 8-coordination sites has been said to contribute to the activity in the partial oxidation of propylene, possibly by stabilizing a pi-allyl intermediate species.

The search, however, continues for new mixed oxides useful as catalysts for partial oxidation and ammoxidation.

BRIEF DESCRIPTION OF THE INVENTION

The present invention includes a mixed oxide of the perovskite structure of the formula $$A_{2-x}Bi_{2x/3}\square_{x/3}C_2O_6$$

wherein A is an alkaline earth metal of atomic number between 20 and 56, C is at least one metal having a number average valence of 4 and x is between about 0.01 and about 1, with metals C and A having ionic radii satisfying the Goldschmidt Tolerance ratio for the perovskite structure, with A and Bi occupying dodecahedral coordination sites and C occupying octahedral coordination sites.

The invention also includes an improvement in a method of oxidizing an acyclic hydrocarbon of 1–10 carbons having at most one olefinic unsaturation by reacting the acyclic hydrocarbon with oxygen in the presence of a solid catalyst to form products having carbon, hydrogen and oxygen; wherein the catalyst is such a mixed oxide.

DETAILED DESCRIPTION OF THE INVENTION

The mixed oxides of the present invention are of the perovskite structure having an alkaline earth metal which is barium, strontium, or calcium, preferably barium in the A-site or dodecahedral coordination site. Trivalent bismuth is also present in the A-site and vacancies are present in the A-site in ratios given by the formula $ABi_{2x/3}\square_{x/3}$ where A is the alkaline earth metal and x is between about 0.01 and about 1, preferably between about 0.01 and about 0.3. The presence of bismuth and vacancies in the A-site has been found to be a necessary prerequisite for catalytic activity.

The C-site or octahedral coordination (6-coordination) site may be occupied by any metal or combination of metals having ionic radius within the range satisfying the Goldschmidt Tolerance Ratio (given the radius of the alkaline earth metal in the A-site) for the perovskite structure and having a number average valence (as described below) of 4. Representative classes include:

(a) equal parts of a divalent metal and a hexavalent metal such as MgTe,
(b) equal parts of a trivalent metal and a pentavalent metal such as $Bi^{+3}Bi^{+5}$,
(c) three parts of a pentavalent metal and one part of a monovalent metal such as $Bi_{4.5}Li_{1.5}$, and
(d) ⅔ parts of a trivalent metal, 1 part of a hexavalent metal and ⅓ part vacant octahedral coordination sites, all parts being by atoms.

In determining the "number average valence" of metals in the octahedral coordination site, it is intended to count vacant sites as having 0 valence so that, for case d, the average is computed as follows:

$$\frac{(\tfrac{2}{3})(3) + (1)(6) + (\tfrac{1}{3})(0)}{\tfrac{2}{3} + 1 + \tfrac{1}{3}} = \frac{8}{2} = 4$$

The mixed oxides of the present invention can be prepared by combining the various metals in the desired proportions by atoms in the form of oxides or precursor compounds, convertable oxides, such as the carbonates, acetates, formates, nitrates, sulfates or sulfites. The oxides or precursors are ground and mixed together and heated in air (at least where any precursors were used) so as to form intimately mixed oxides which form the perovskite structure.

EXAMPLES 1–7

Preparation of Mixed Oxides

Six mixed oxides were prepared by combining the oxides and/or carbonates or other precursors of barium, bismuth and, in some cases, other metals such as tellurium, magnesium, lithium and tantalum. These precursors were combined in proportions giving the relative atom % of barium and bismuth (as a percentage of total metal) shown in Table 1 for (C1), (2), (3), (4), (5) and (6). The remaining atom % was tellurium in (C1)(27.3%) and (2)(27.6%); was magnesium and tellurium (25.3% each) in (3) and was lithium (12.7%) in (5). Mixed oxides (4) and (C6) had exclusively barium and bismuth as metals.

Each of the mixtures was heated 3 times to 600°–950° C. for 24 hours per cycle and ground before each heating cycle. The heating was conducted in air in all examples.

Each mixed oxide was then examined by powder x-ray diffraction techniques with monochromatic CuK radiation (wavelength 15.416 nm) and the crystallographic ordering detected by the appearance of superstructure reflections. It was determined that such mixed oxide had assumed a perovskite configuration as described in F. S. Galasso, *Structure, Properties and Preparation of Perovskite Type Compounds* (Pergamon Press 1969) with barium or barium and some bismuth in the dodecahedral coordination sites as indicated by the column "A-site Metals" in Table 1. Where bismuth was present in these sites, vacancies were also present in the A-sites at an apparent ratio of A-site bismuth to A-site vacancies of about 2:1 (as indicated by the single asterisks). In addition, metals present in the octahedral coordination sites of the perovskite structure were noted as indicated by the column "B-site Metals" in Table 1. As indicated by asterisks, about one-sixth of the B-sites were determined to be vacant in (C1) and (2), as indicated by the double asterisks.

It will thus be appreciated that only the four mixed oxides having bismuth and single asterisks had dodecahedral coordination sites occupied in part by bismuth and in part vacant. Among these four, (2), (4) and (5) had additional bismuth in B-sites and (2) had additional vacancies in B-sites. (C1) and (C6) were controls which lacked bismuth and vacancies in the A-sites, although (C1) did have bismuth and vacancies in B-sites. The narrowness of these distinctions can be seen by comparing the overall composition of (4) with (C6).

For comparison a lead-bismuth-molybdenum oxide of the scheelite structure was prepared in accordance with A. W. Sleight et. al., *J. Catal.*, vol. 35, pp. 401 et. seq. (1974) and A. W. Sleight pp. 181–208 of *Advanced Materials in Catalysts* (J. L. Burton et. al. eds., Academic Press 1977). Its stoichiometry was about $Pb_{0.85}Bi_{0.1}MoO_4$ and it was determined to have a scheelite structure with lead and bismuth being in 8-coordination sites (A-sites) and molybdenum being in tetrahedral coordination sites (B-sites).

TABLE 1
MIXED OXIDES

| Mixed Oxides % Ba % Bi (atom % of Metal) | A-site Metals | B-site Metals |
|---|---|---|
| C1) $Ba_6Bi_2Te_3O_{18}$ 54.5% 18.2% | $Ba_6$ | $Bi_2Te_3$** |
| 2) $Ba_{5.55}Bi_{2.3}Te_3O_{18}$ 51.2% 21.2% | $Ba_{5.55}Bi_{0.3}$* | $Bi_2Te_3$** |
| 3) $Ba_{5.55}Bi_{0.3}Mg_3Te_3O_{18}$ 46.8% 2.5% | $Ba_{5.55}Bi_{0.3}$* | $Mg_3Te_3$ |
| 4) $Ba_{5.55}Bi_{6.3}O_{18}$ 46.8% 53.2% | $Ba_{5.55}Bi_{0.3}$* | $Bi_3{}^{+3}Bi_3{}^{+5}$ |
| 5) $Ba_{5.55}Bi_{4.8}Li_{1.5}O_{18}$ 46.8% 40.5% | $Ba_{5.55}Bi_{0.3}$* | $Bi_{4.5}Li_{1.5}$ |
| C6) $Ba_6Bi_6O_{18}$ 50% 50% | $Ba_6$ | $Bi_3{}^{+3}Bi_3{}^{+5}$ |
| C7) $Pb_{0.85}Bi_{0.1}MoO_4$ — 5.1% | $Pb_{1.7}Bi_{0.2}$*** | $Mo_2$ |

*0.05 A-site vacancies per 1.85 Ba (one-fortieth of sites vacant)
**One-sixth of B-sites vacant
***0.1 A-site vacancies per 1.7 Pb and 0.2 Bi (one-twentieth of sites vacant)

EXAMPLE 8

Oxidation of Propane

The seven mixed oxides prepared in Examples 1–7 were tested for catalytic activity to partially oxidize propane to products of one, two or three carbons with hydrogen and oxygen.

The reactor system employed comprised essentially a reactor tube containing the catalyst. The tube was mounted in a controlled temperature furnace. One end of the tube was fed with the starting materials and at the other end the reaction products were withdrawn. The reactor was mounted to permit the upward flow of the reactants over a catalyst of one of Examples 1–8 with the products exiting into a gas chromatograph. Gas phase samples were collected by air actuated sample valves in 1 cc loops. All the lines after the reactor were heated to prevent condensation. Samples were alternately collected before and after passing over the catalyst. This provided the reactant versus product analysis necessary for mass-balancing the product stream.

A separately controlled furnace surrounded the concentric up-flow/plug-flow reactor. The temperature of the reactor was controlled by a set of manually operated potentiometers. These potentiometers were sequenced in turn by a clock-stepping switch. In this way a suitable sequence of temperatures was programmed. At each temperature, an exit followed by an inlet analysis was performed.

In a typical study the temperature was raised from room temperature to 300° C. under reactant feed. Samples were taken at several temperatures between 300° C. and 525° C. The product analysis was visually inspected to look for partial oxidation products. As soon as substantial conversion (usually of the limiting reactant-oxygen) was seen, the temperature was held constant for two or three analyses. Then the temperature was lowered again, in 20° increments, to 300° C. This last stage was usually done automatically. Following this, the specific partial oxidation activity was estimated both visually from the gas chromatographic analysis and by comparing the computer integrated gas chromatographic peaks. If warranted, the activity was checked at specific temperatures. Thermal restoration of activity was confirmed. The catalyst was removed from the furnace after cooling and replaced with a new catalyst to be studied.

Analysis was performed by a two column gas chromatographic unit. One column (molecular sieve) was used for the low boiling reactants and products ($N_2$, $O_2$, $CH_4$, CO) while the second column (10 feet or 3.67 m of PORAPAC Q packing at temperature ranging from 50° C. at the inlet to 210° C. at the outlet) was used for high boiling products. In addition to a dual pen recorder, an online computer (EAI) integrated the sample gas chromatographic peaks.

The results of tests with each mixed oxide at several temperatures are summarized in Table 2. In order to explain the terms used, a detailed analysis of one experiment is shown in Table 3. In this experiment a feed of 51.3 mole % propane, 23.4 mole % oxygen and 25.3 mole % nitrogen was passed through catalyst (2) at 390° C. and the materials indicated in Table 3 were detected in the exit. The distribution by mole % is shown in the first line. It can be seen that, of the 51.3% propane fed, 20.6% was converted [(51.3−40.7)/51.3]. The moles of carbon-containing products were then normalized based upon number of carbons and compared to the converted propane to give selectivities as indicated in the second line. The methane, ethylene, ethane and propylene (or whichever of these were observed in an effluent) are together considered to be the selectivity to cracking (3+12=15%). The methanol, acetaldehyde and acrolein are together considered to be partial oxidation products (16+12+8=36%). Of the partial oxidation products, the proportions of each product is considered to be the specific selectivity indicated in the following lines.

It can be seen, by comparing Table 3 with the fourth column of Table 2, how Table 3 summarizes the experiment. Similar calculations were used for each other column in Table 2.

TABLE 2

Oxidation of Propane

| Catalyst | C1 | C1 | 2 | 2 | 2 | 2 | 2 |
|---|---|---|---|---|---|---|---|
| Temperature | 350 | 480 | 365 | 390 | 425 | 475 | 490 |
| HC/O₂ (x:1) | 2 | 2 | 2 | 2 | 2 | 2 | 2 |
| HC Conversion (%) | | | 28.3 | 20.8 | 20.7 | 42.2 | 47.5 |
| Selectivity to | | | | | | | |
| CO | | | 26 | 43 | 38 | 23 | 22 |
| CO₂ | | | 6 | 6 | 6 | 1 | 1 |
| Cracking | insignificant | | 30 | 15 | 20 | 62 | 66 |
| Part. Oxid. | | | 30 | 36 | 36 | 14 | 11 |
| Spec. Sel. to | | | | | | | |
| CH₃OH | | | 34 | 45 | 32 | 9 | 6 |
| CH₂O | | | — | — | — | — | — |
| CH₃CH₂OH | | | — | — | — | — | — |
| CH₃CHO | | | 20 | 34 | 32 | 16 | 8 |

TABLE 2-continued

Oxidation of Propane

| CH₃CH₂CHO | | | — | — | — | 21 | 45 |
|---|---|---|---|---|---|---|---|
| CH₂=CHCHO | | | 9 | 21 | 36 | 54 | 41 |
| HCOOH | | | 10 | — | — | — | — |
| CH₃CH₂COOH | | | 30 | — | — | — | — |

| Catalyst | 3 | 3 | 3 | 4 | 4 | 4 |
|---|---|---|---|---|---|---|
| Temperature °C. | 445 | 405 | 375 | 465 | 430 | 412 |
| HC/O₂ | 2 | 2 | 2 | 2 | 2 | 2 |
| HC Conversion | 37 | 28 | 26 | 27 | 23 | 23 |
| Selectivity to | | | | | | |
| CO | 24 | 30 | 34 | 43 | 50 | 50 |
| CO₂ | 4 | 5 | 6 | 6 | 9 | 8 |
| Cracking | 55 | 40 | 32 | 26 | 16 | 14 |
| Part. Oxid. | 17 | 25 | 28 | 25 | 25 | 28 |
| Spec. Sel. to | | | | | | |
| CH₃OH | 29 | 44 | 45 | 39 | 70 | 58 |
| CH₂O | — | — | — | — | — | — |
| CH₃CH₂OH | 3 | 4 | 2 | — | — | — |
| CH₃CHO | 23 | 27 | 35 | 16 | 30 | 42 |
| CH₃CH₂CHO | 24 | 9 | 7 | 20 | — | — |
| CH₂=CHCHO | 21 | 16 | 11 | 25 | — | — |

| Catalyst | 5 | 5 | C6 | C7 |
|---|---|---|---|---|
| Temperature °C. | 475 | 442 | not activated | 480 |
| HC/O₂ | 2 | 2 | | 2 |
| HC Conversion | 34 | 30 | | 33 |
| Selectivity to | | | | |
| CO | 29 | 31 | | 33 |
| CO₂ | 5 | 5 | | 4 |
| Cracking | 51 | 44 | | 47 |
| Part. Oxid. | 15 | 20 | | 16 |
| Spec. Sel. to | | | | |
| CH₃OH | 36 | 42 | | 55 |
| CH₂O | — | — | | — |
| CH₃CH₂OH | 2 | 2 | | — |
| CH₃CHO | 21 | 22 | | 44 |
| CH₃CH₂CHO | 27 | 11 | | 14 |
| CH₂=CHCHO | 14 | 23 | | 2 |

TABLE 3

Oxidation of Propane With Oxide (2) at 390° C.

| Component | N₂ | CO | CO₂ | CH₄ | C₂H₄ |
|---|---|---|---|---|---|
| Exit Stream (mole %) | 25.3 | 13.8 | 2.0 | 0.9 | 1.9 |
| Selectivity | — | 43 | 6 | 3 | 12 |

| Component | C₃H₈ | H₂O | CH₃OH | CH₃CHO | CH₂=CHCHO |
|---|---|---|---|---|---|
| Exit Stream (mole %) | 40.7 | 21.3 | 5.0 | 1.9 | 0.8 |
| Selectivity | — | — | 16 | 12 | 8 |
| Specific Selectivity | — | — | 45 | 34 | 21 |

We claim:

1. In a method of oxidizing an acyclic hydrocarbon of 1-10 carbons having at most one olefinic unsaturation by reacting in the vapor phase an acyclic hydrocarbon with oxygen in the presence of a solid catalyst to form products having carbon, hydrogen and oxygen, the improvement wherein the catalyst is a mixed oxide of the perovskite structure of the formula $A_{2-x}Bi_{2x/3}\square_{x/3}C_2O_6$ wherein A is an alkaline earth metal of atomic number between 20 and 56 which is calcium, strontium or barium, $C_2$ is at least one metal having a number average valence of 4 selected from the group consisting of:

(a) a mixture of equal parts, by atoms, of a divalent metal and a hexavalent metal;

(b) a mixture of equal parts, by means of atoms, of a trivalent metal and a pentavalent metal;

(c) a mixture of 3 parts, by atoms, of a pentavalent metal and 1 part, by atoms, of a monovalent metal; and (d) a mixture of $\frac{2}{3}$ parts of a trivalent metal, 1 part of a hexavalent metal and $\frac{1}{3}$ part vacant octahedral coordination site, all by atoms;

and x is between about 0.01 and about 1, with the metals C and A having ionic radii satisfying the Goldschmidt Tolerance ratio for the perovskite structure, with A and Bi occupying dodecahedral coordination sites and C occupying octahedral coordination sites.

2. The method of claim 1 wherein x is between about 0.01 and about 0.3.

3. The method of claim 1 wherein A is barium.

4. The method of claim 1 or 3 wherein $C_2$ is a mixture of equal parts, by atoms, of a divalent metal and a hexavalent metal.

5. The method of claim 4 wherein $C_2$ is MgTe.

6. The method of claim 1 or 3 wherein $C_2$ is a mixture of equal parts, by atoms, of a trivalent metal and a pentavalent metal.

7. The method of claim 6 wherein $C_2$ is $Bi^{+3}Bi^{+5}$.

8. The method of claim 1 or 3 wherein $C_2$ is a mixture of 3 parts, by atoms, of a pentavalent metal and 1 part, by atoms, of a monovalent metal.

9. The method of claim 8 wherein $C_2$ is $Bi_{4.5}Li_{1.5}$.

10. The method of claim 1 or 3 wherein $C_2$ is a mixture of $\frac{2}{3}$ parts of a trivalent metal, 1 part of a hexavalent metal and $\frac{1}{3}$ part vacant octahedral coordination site, all by atoms.

* * * * *